US 9,801,585 B2

(12) United States Patent
Shah et al.

(10) Patent No.: US 9,801,585 B2
(45) Date of Patent: Oct. 31, 2017

(54) ELECTROCARDIOGRAM NOISE REDUCTION

(71) Applicant: Biosense Webster (Israel) Ltd., Yokneam (IL)

(72) Inventors: Kruti Shah, Mission Viejo, CA (US); Alexander Lifshitz, Arcadia, CA (US); Itzhak Fang, Irvine, CA (US)

(73) Assignee: BIOSENSE WEBSTER (ISRAEL) LTD., Yokneam, IL (US)

( * ) Notice: Subject to any disclaimer, the term of this patent is extended or adjusted under 35 U.S.C. 154(b) by 0 days.

(21) Appl. No.: 14/587,538

(22) Filed: Dec. 31, 2014

(65) Prior Publication Data

US 2016/0183876 A1 Jun. 30, 2016

(51) Int. Cl.
*A61B 5/00* (2006.01)
*A61B 5/0402* (2006.01)
*A61B 5/042* (2006.01)
*A61B 18/14* (2006.01)

(52) U.S. Cl.
CPC .......... *A61B 5/6852* (2013.01); *A61B 5/0402* (2013.01); *A61B 5/0422* (2013.01); *A61B 5/7217* (2013.01); *A61B 18/1492* (2013.01); *A61B 2018/1472* (2013.01); *A61B 2562/182* (2013.01)

(58) Field of Classification Search
CPC .................................................... A61B 5/6852
USPC .......................................................... 600/509
See application file for complete search history.

(56) References Cited

U.S. PATENT DOCUMENTS

| 4,790,311 A * | 12/1988 | Ruiz .................... A61B 18/082 606/28 |
| 5,843,076 A * | 12/1998 | Webster, Jr. ........ A61B 18/1492 600/439 |
| 6,226,542 B1 * | 5/2001 | Reisfeld ............. A61B 5/04011 600/407 |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 8,478,383 B2 | 7/2013 | Bar-Tal et al. |

(Continued)

FOREIGN PATENT DOCUMENTS

EP 2319412 A1 5/2011

*Primary Examiner* — Nadia A Mahmood
(74) *Attorney, Agent, or Firm* — Roberts Mlotkowski; Safran Cole & Calderon, P.C.

(57) ABSTRACT

A catheterization system that includes an electrophysiologic (EP) catheter which has a lumen receiving an electrically conductive fluid delivered by a hydraulic line that is acted upon by a peristaltic pump advantageously avoids noise in intracardiac ECG signal recordings by using an electrical connection to short triboelectrical charge carried by the conductive fluid in the hydraulic line to an existing analog ground in the system. In one embodiment, the electrical connection includes an electrically conductive wire housed in the control handle and configured to provide electrical connection between the fluid and a pin on a printed circuit board housed in the control handle that is electrically connected to the analog ground. In another embodiment, the electrical connection shorts the electrically conductive fluid proximal of the control handle of the catheter.

18 Claims, 8 Drawing Sheets

(56) References Cited

U.S. PATENT DOCUMENTS

| | | |
|---|---|---|
| 8,956,353 B2 | 2/2015 | Govari et al. |
| 2013/0158379 A1 | 6/2013 | Selkee |
| 2014/0343434 A1 | 11/2014 | Elbert |
| 2014/0378902 A1 | 12/2014 | Saba |

* cited by examiner

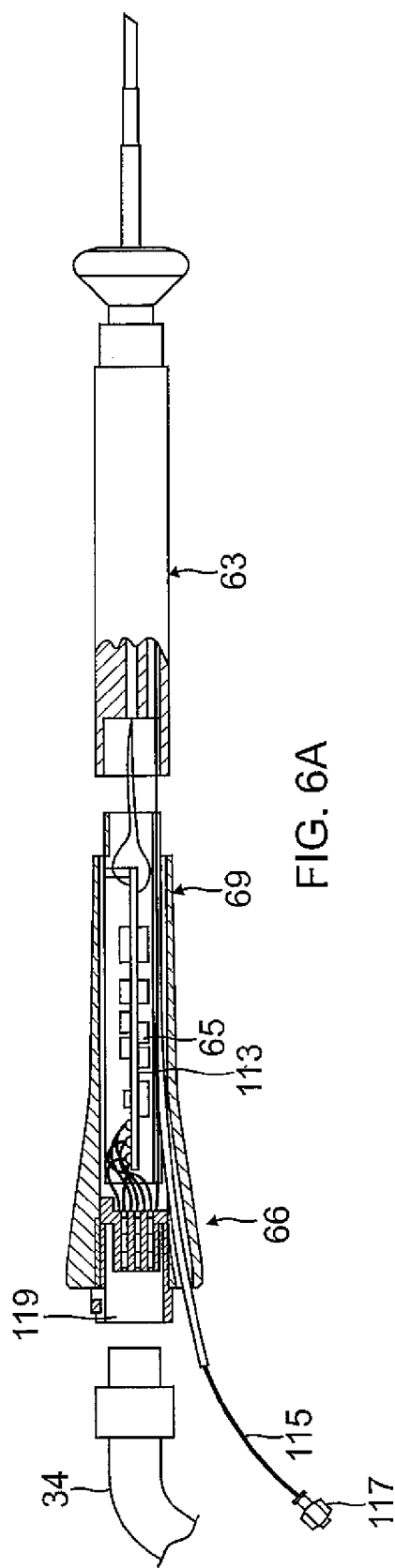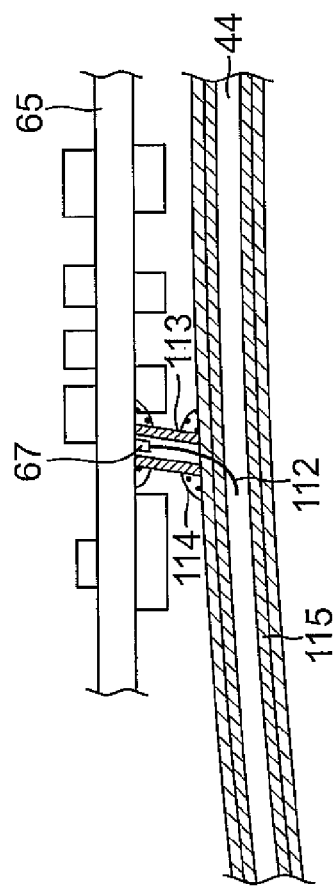
FIG. 6A
FIG. 6B

ELECTROCARDIOGRAM NOISE REDUCTION

FIELD OF INVENTION

This invention relates to medical catheterization. More particularly, this invention relates to electrocardiographic monitoring during medical catheterization procedures.

BACKGROUND

The meanings of certain acronyms and abbreviations used herein are given in Table 1.

TABLE 1

Acronyms and Abbreviations

| ECG | Electrocardiogram |
| PIU | Patient Interface Unit |
| RF | Radiofrequency |

Medical catheterizations are routinely carried out today. For example, in cases of cardiac arrhythmias, such as atrial fibrillation, which occur when regions of cardiac tissue abnormally conduct electric signals. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure. Commonly assigned application Ser. No. 13/339,782 (now U.S. Pat No. 8,956,353), which is herein incorporated by reference, discloses the use of an irrigation pump to cause irrigation fluid to flow through a lumen of the catheter in order to cool the ablation site.

A typical catheterization system includes a catheter which is inserted through a patient's vascular system into a chamber or vascular structure of the heart. The catheter's distal tip is brought into contact with the heart wall for obtaining electrical and positional information that is processed by a console that includes a processor for generating activation maps, anatomical positional information and other functional images. The system typically includes an electrocardiogram (ECG) monitor coupled to receive signals from one or more body surface electrodes. The ECG signal is typically received through an interface with the console, e.g., a patient interface unit having an analog input and an isolated ground may be used to provide an ECG synchronization signal to the console.

An electrically conductive fluid, e.g., saline, is delivered through a lumen in the catheter from a reservoir via a hydraulic line. The lumen terminates in exit pores through which the liquids emerge to cool an ablating electrode at the distal portion of the catheter and also the tissue ablation site. A peristaltic pump is connected to the hydraulic line and causes the fluid to be delivered to the catheter at a desired rate. One difficulty with such an arrangement is that operation of equipment in the environment, e.g., the pump produces electrical effects, which produce noise that can be picked up by the hydraulic line and can interfere with the analysis and display of the intracardiac ECG on the monitor. The electrical emissions or signals are usually observed in ECG leads connected to a patient who is being transfused or infused with the electrically conductive solution. Any currents that flow in the patient's body as a result of this potential are sensed as characteristic noise added to the ECG signals.

This noise has been observed in patients connected to a peristaltic pump for cardiac assist, dialysis treatments and irrigation of an ablation catheter used in treating cardiac arrhythmias. Many sources have been proposed as sources for the noise, some focusing on the pump itself.

Without being bound by any particular theory, the following discussion as set forth in U.S. patent application Ser. No. 13/327,448 (now U.S. Pat. No. 9,101,269), filed Dec. 15, 2001, entitled ELECTROGRAM NOISE REDUCTION, the entire content of which is incorporated herein by reference, is offered to facilitate understanding of the various embodiments described and disclosed herein: In one respect the hydraulic line may function as a receiving antenna that collects noise from the surrounding environment and may constitutes one source of the noise. In another respect, the pump may be another source of electrical noise, created by a triboelectric effect, whereby an induced charge is created on the surface of flexible tubing used in the pump and on the surface of the rotor surfaces used to compress the tubing. The rubbing or deforming action of the rotor against the tubing surface displaces electrical charge. Some of the charge is collected on the rotor and some is collected on the tubing surface. The tubing wall is generally an insulator, so that the external charge on the outside surface of the tube is induced on the inside of the tubing bore if the fluid in the tubing is an electrical conductor. In consequence, a generator potential appears between the electrically conductive fluid and the pump rotor. Any electrical circuit connecting these two points allows current to flow. Such current, if sensed or intercepted by the EKG circuitry, produces undesirable signals on the EKG tracing that are perceived as "ECG noise" by the operator. Because the triboelectric potential appears in series with the capacitance of the external and internal tubing walls, which are generally insulators (plastic), the triboelectric current has bursty characteristics.

Additionally or alternatively, the observed current may arise from a piezoelectric effect in the tubing walls. Further additionally or alternatively, there appears to be a strong amplification mechanism resulting from the motion of the tubing walls as they are squeezed between the rotor rollers and the pump race, causing a dynamic change in tubing capacitance, which is in series with the triboelectric charge.

The noise, as observed on intracardiac ECG recordings, appears as spikes, making the ECG signals difficult to interpret, and these spikes (typically ranging between about 0.05 mV and 0.2 mV) can even be confused as ECG waves themselves. Additionally, a fast Fourier transform applied to the noise to obtain its power spectrum finds component sinusoids at repetition frequencies equal to the impact rate of the rotor rollers (N) on the tubing surface along with higher harmonics. The repetition frequencies are dependent on the number of rollers in a rotor, and are to be distinguished from the rotor rotation rate itself.

FIGS. 8A-8C illustrate actual ECG recordings with repetitive "spikes" (designated by arrows) in intracardiac ECG signals during ablation procedures using SmartAblate Pump. Analyzing the recordings, it was determined that the frequency of the spikes is proportional to the speed of pump motor (or proportional to the flow rate), such that, for example, for 30 ml/min the spikes occur at about 85 ms time intervals, and for 15 ml/sec the spikes occur at about 170 ms (double the 85 ms time interval). It also appeared that the amplitude of the spikes increased with flow rate (though no linearly), such that the effect was clearly observed only for high flow rates and was indistinguishable for low rates used during mapping/navigation phases. The reported amplitudes of the spikes (measured peak-to-peak) were in the range of about 100-200 µV. It is understood that the noise differs for different pump designs. Time between peaks and peak-to-peak voltage can vary.

Treatments to reduce the noise have included lining the pump roller and pump bed, coating the pump hydraulic line with an antistatic chemical, and/or wetting the contact surfaces of these components. However, the reduction tends to be insignificant and/or temporary.

The aforementioned U.S. patent application Ser. No. 13/327,448 (now U.S. Pat. No. 9,101,269) describes a hydraulic line having an outer portion coated with a material or an antistatic chemical, including the portion contacting the outer surface with the rotating element of the pump. The material contains liquid water and an ionic surfactant. The antistatic chemical may be selected from the group consisting of soap water, saline and water. In addition, the contacting portion of an outer surface of the hydraulic line may be coated with an electrical conductor, for example, indium tin oxide or aluminum foil. The hydraulic line may also be impregnated with the anti-static chemical.

The aforementioned U.S. patent application Ser. No. 131327,448 (now U.S. Pat. No. 9,101,269) also describes a system wherein a catheter has a lumen for passing an electrically conductive fluid therethrough to exit the catheter at its distal portion, the lumen connectable to an irrigation pump to form a fluid communication therewith. A fluid reservoir is connected to the lumen for supplying the electrically conductive fluid to the catheter. Electrocardiogram circuitry is connectable to the subject for monitoring electrical activity in the heart. An electrically conductive cable links the electrically conductive fluid to an electrode that is in contact with the subject. According to an aspect of the system, the catheter has mapping electrodes disposed on the distal portion and the electrode is located on the catheter proximal to the mapping electrodes. According to a further aspect of the system, the electrode is located on a second catheter that is introduced into the subject. According to one aspect of the system, the catheter has an inlet port, and a connector electrically contacts the electrically conductive fluid at the inlet port, and connects the electrically conductive fluid to a patient ground. According to another aspect of the system, the electrically conductive cable is electrically connected to the electrically conductive fluid downstream of the irrigation pump. According to an additional aspect of the system, the electrically conductive cable is a metallically shielded cable.

However, the use of an additional external connection cable increases the burden on an electrophysiology professional by a typical catheterization system which already employs numerous connectors and cables to and from equipment pieces and the patient. Moreover, the use of a cable that links the electrically conductive fluid to an electrode that is in contact with the patient may render the system's ability to reduce ECG noise dependent on a number of factors, including the quality of the connection between the electrode and patient, the location of the electrode, and the impedance of the patient's body, which differs from patient to patient. In addition, any added or modified electrical link within the catheterization system may subvert the equipment grounding conductor paths necessary for the system circuit to meet safety requirements.

Accordingly, there is a desire for a catheterization system that reduces or eliminates ECG noise. There is a desire that the noise reduction or elimination be accomplished without compromising patient safety or regard to factors, including the quality of the connection between the electrodes and patient, the location of the electrode on the patient, and the impedance of the patient's body, which differs from patient to patient. There is also a desire for a catheterization system which avoids the use of any additional lengthy cable, especially one that extends between the patient and the fluid source or fluid pump which can tangle or disrupt workflow of the attending medical professionals.

SUMMARY OF THE INVENTION

The present invention is directed to a catheterization system that includes an electrophysiologic (EP) catheter which has a lumen receiving an electrically conductive fluid delivered by a hydraulic line that is acted upon by a peristaltic pump. The present invention recognizes that pump action on the hydraulic line produces a triboelectrical charge that is carried by the conductive fluid in the hydraulic line which can appear as noise in patient ECG recordings detected by an electrode on the catheter. Advantageously, the present invention reduces, if not eliminates, the noise by using an existing isolated ground in the catherization system to reroute the tribo electric charge away from the conductive fluid before the fluid reaches or comes in contact with the catheter electrode. By providing an electrical connection between the existing isolated ground and the conductive fluid at a location proximal of the portion of the catheter in the patient's body, including electrode(s) at the distal end of the catheter, the triboelectric charge bypasses the catheter electrode which enables the conductive fluid to enter the patient's body without carrying the triboelectric charge. The electrical "short" or connection to the isolated ground is configured advantageously upstream of any electrode or port in the catheter through which the conductive fluid enters the patient. Thus, the patient's body remains free of the triboelectric charge that would otherwise disrupt intracardiac signals detected by the catheterization system, or any ECG detection system. The system of the present invention provides an alternate pathway for the triboelectric charge that avoids disruption to and detection by the catheter electrodes or any other electrodes in contact with the patient's body. The embodiments of the present invention provide an electrical connection that avoids another lengthy cable for the EP operator to connect and monitor, without compromising the safety of the patient.

In some embodiments, the electrical connection shorts the electrically conductive fluid inside a control handle of the catheter. In some more detailed embodiments, the electrical connection includes an electrically conductive wire that is housed in the control handle and configured to provide electrical connection between the fluid and a pin on a printed circuit board housed in the control handle that is electrically connected to the isolated ground.

In some embodiments, the electrical connection shorts the electrically conductive fluid proximal of the control handle of the catheter. In some more detailed embodiments, a wire that extends into the control handle and is electrically connected to the isolated ground has a divergence or split proximal of the control handle into a side wire that is adapted for connection to a luer hub mounted on a distal end of the hydraulic line and adapted to pass the electrically conductive fluid to an irrigation tubing of the catheter.

The present invention is not limited to the effects of triboelectric charge but rather the present invention can exclude any other noise that may occur due to hydraulic line, for example, mechanical pressure waves generated in tubing due to back pressure, mechanical pressure waves in catheter lumen due to back pressure, frictional noise, etc.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 6A is a side view of a catheter control handle of the system of FIG. 1.

FIG. 6B is a detailed view of a portion of the catheter control handle of FIG. 6A.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as USB memory, hard drive, electronic media or CD-ROM. The code may be distributed on such media, or may be distributed to us-ers from the memory or storage of one computer system over a network of some type to storage devices on other computer systems for use by users of such other systems.

Definitions

"Noise" is a disturbance, including a random and persistent disturbance that obscures or reduces the clarity of a signal.

System Description

Figure 1:
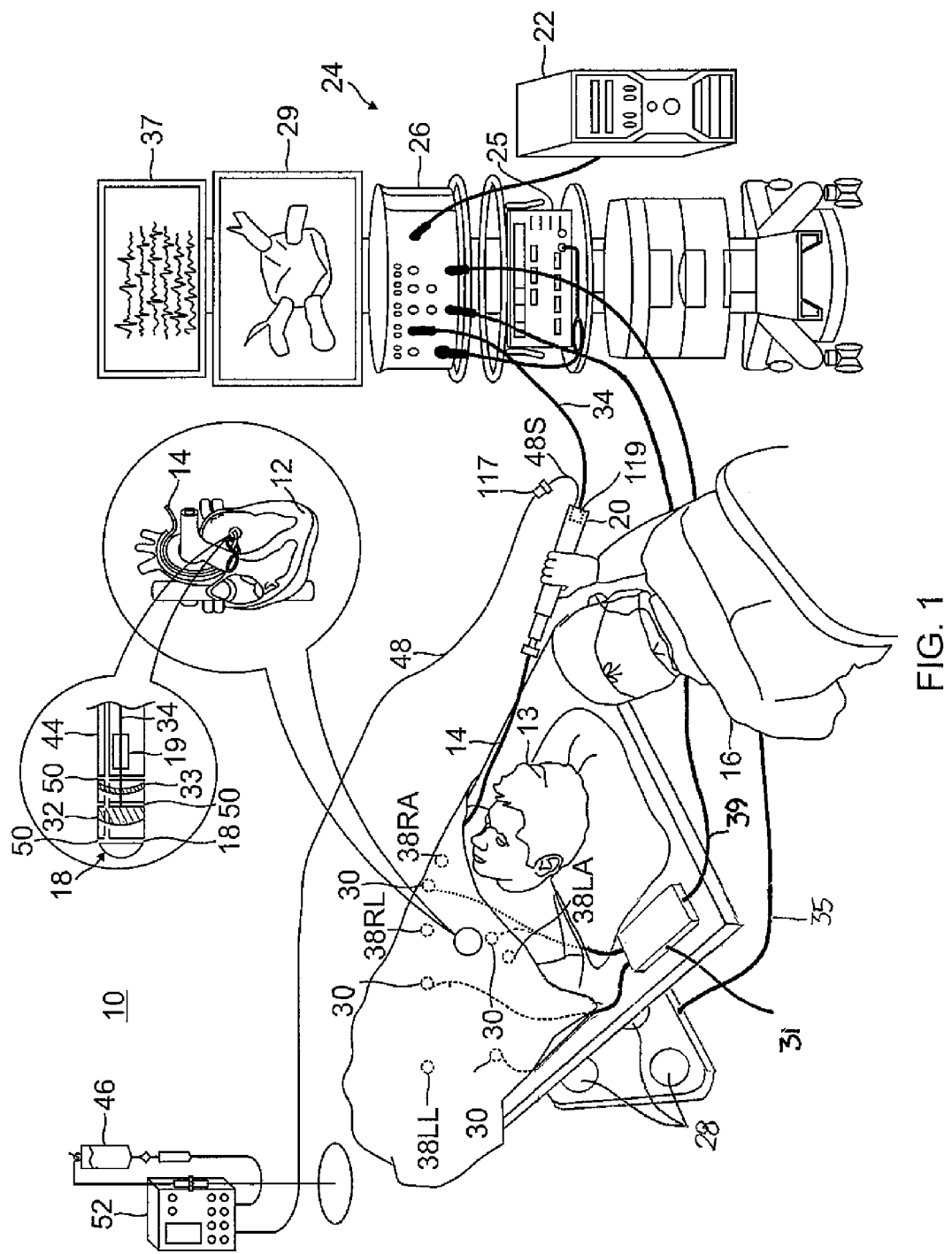
FIG. 1 is a pictorial illustration of a system for performing catheterization procedures on a heart of a living subject, which is constructed and operative in accordance with an embodiment of the present invention.

Turning now to the drawings, reference is initially made to FIG. 1, which is a pictorial illustration of a system 10 for performing exemplary catheterization procedures on a heart 12 of a living subject or patient 13, which is constructed and operative in accordance with a disclosed embodiment of the invention. The system comprises a catheter 14, which is percutaneously inserted by an electrophysiologist or operator 16 through the patient's vascular system into a chamber or vascular structure of the heart 12. The catheter 14 has a distal tip 18 carrying one or more electrodes 32 and 33, and a control handle 20 by which the operator can manipulate to steer and deflect the catheter.

The operator 16 brings the catheter's distal tip 18 into contact with the heart wall. Electrical activation maps, anatomic positional information, i.e., of the distal portion of the catheter, and other functional images may then be prepared using a console 24, according to the methods disclosed in U.S. Pat. Nos. 6,226,542, and 6,301,496, and in commonly assigned U.S. Pat. No. 6,892,091, whose entire disclosures are herein incorporated by reference. One commercial product embodying elements of the console 24 is the CARTO® 3 System, available from Biosense Webster, Inc., 3333 Diamond Canyon Road, Diamond Bar, Calif. 91765, which performs catheter localization and produces 3-D electroanatomic maps of the heart as required. This system may be modified by those skilled in the art to embody the principles of the invention described herein.

Areas determined to be abnormal, for example by evaluation of electrical activation maps, can be targeted and ablated by application of thermal energy, e.g., by passage of radiofrequency electrical current from a radiofrequency (RF) generator 25 of the console 24 through a cable 34 providing current to the catheter, including the ablation electrode 32 at the distal tip 18, which apply the radiofrequency energy to target tissue. The energy is absorbed in the tissue, heating it to a point at which it permanently loses its electrical excitability. When successful, this procedure creates non-conducting lesions in the cardiac tissue, which disrupt the abnormal electrical pathway causing the arrhythmia.

The console 24 typically contains one or more ablation power generators 25. The catheter 14 is adapted to conduct ablative energy to the heart using radiofrequency energy. Such methods are disclosed in commonly assigned U.S. Pat. Nos. 6,814,733, 6,997,924, and 7,156,816, which are herein incorporated by reference. Ablation energy is conveyed from RF generator 25 to the heart 12 through the catheter tip, including irrigated ablation electrode 32, via cable 34 which is connected to the console 24. Pacing signals and other control signals may also be conveyed from the console 24 through the cable 34 and the ablation electrode 32 to the heart 12. Moreover, electrical signals (for example, intracardiac ECG signals) are conveyed from the heart 12 to the console 24 through the catheter tip, including the irrigated ablation electrode 32 and one or more nonirrigated ring electrodes 33, and the cable 34. A temperature sensor (not shown), typically a thermocouple or thermistor, may be mounted on or near each of the catheter electrodes.

As part of the system 10, ECG body surface patches, including at least patches 38RA, 38LA, 38RL and 38LL are affixed to the patient's body. While the catheter electrodes 32 and 33 are sensing intracardiac ECG signals, a plurality of electrodes in the ECG body surface patches 38RA, 38LA, 38RL and 38LL measure ECG signals across the heart and torso to provide reference signals for the intracardiac ECG signals measured by the catheter electrodes.

As part of the catheter localization capabilities of the console 24, a magnetic field is generated around the patient 13, for example, by a location pad containing magnetic field generator coils 28 that is placed under the patient. The magnetic fields generated by coils 28 generate electrical signals in coils of an electromagnetic (EM) sensor 19 located in the distal tip 18 of catheter 14. The electrical signals are conveyed to the console 24 which includes a processor 22 that analyzes the signals so as to determine the coordinates of the position and orientation of catheter.

As also part of the catheter localization capabilities of the console 24, the catheter electrodes 32 and/or 33 are connected by lead wires in the catheter 24 and the cable 34 to current and voltage measurement circuitry in the processor 22. The processor 22 and the console 24 are also connected by wires 35 to a plurality of body surface electrodes 30, which may be any type of body electrodes known in the art, such as button electrodes, needle electrodes, subcutaneous probes, or patch electrodes. The body surface electrodes 30 are typically in galvanic contact with the body surface of the patient 13 and receive body surface currents therefrom. The body surface electrodes 30 may be adhesive skin patches generically referred to as active current location (ACL patches) and may be placed at any convenient locations on the body surface of the patient 13 in the vicinity of the catheter 14. In the disclosed embodiment, there are six ACL patches 30, three affixed on the anterior surface of the patient's torso and three on the posterior surface. The console 24 comprises voltage generators which are connected via a patch unit 31 and cable 39 to the ACL patches 30 which the processor 22 uses to measure impedance of the patient tissue at the location of the patches 30. Accordingly, the console 24 uses both magnetic-based position sensing and impedance-based measurements for catheter localization, as described in U.S. Pat. No. 7,536,218, issued to Govari et al., and U.S. Pat. No. 8,478383, issued to Bar-Tal et al., the entire content of both of which are herein incorporated by reference.

As noted above, the catheter 14 is coupled to the console 24, which enables the operator 16 to observe and regulate the functions of the catheter 14. The processor 22 and/or the console 24 include appropriate signal processing circuits and is coupled to drive a monitor 29 to display visual imagery including the 3-D electroanatomical maps. The signal processing circuits typically receive, amplify, filter and digitize signals from the catheter 14, including signals generated by the above-noted electrodes 32 and 33 and EM sensor 19.

Figure 5:
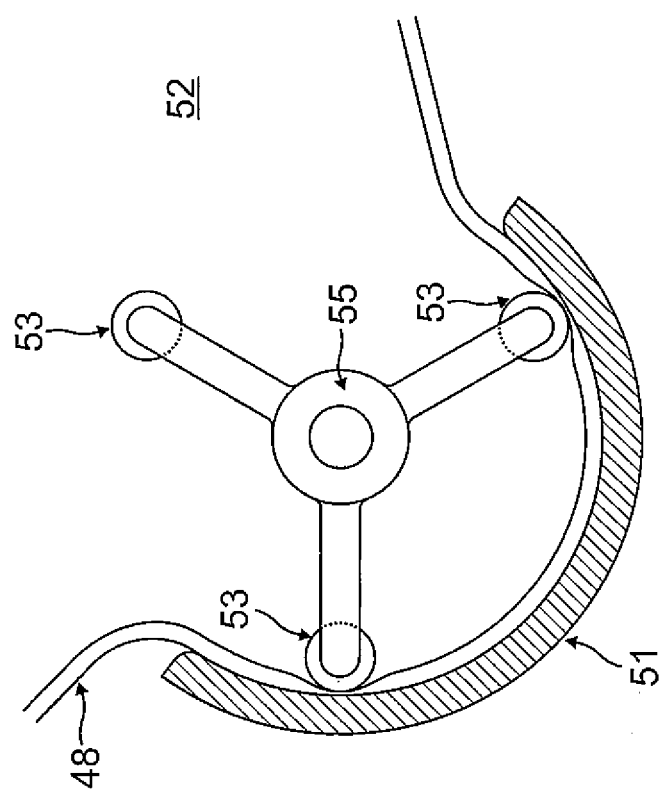
FIG. 5 is a schematic illustration of a pump device.

To irrigate the catheter, including the ablation electrode 32, an electrically conductive fluid, e.g., saline, is delivered through a lumen 44 in the catheter 14 from a reservoir 46 via a hydraulic line 48. The electrically conductive fluid is sometimes referred to herein as "saline" for convenience, it being understood that this is by way of example and not of limitation. The lumen 44 terminates in exit pores 50 at the distal tip 18 and in the ablation electrode 32 through which the fluid emerges to cool the tip 18, the electrode 32 and the ablation site. A peristaltic pump 52 is connected to the hydraulic line 48 and causes the fluid to be delivered to the catheter 14 at a desired rate through an entrance port, e.g., a luer hub 117, at the proximal end of a lumened irrigation tubing 115 of the catheter 14. As shown in FIG. 5, the peristaltic pump 52 has a pump bed 51 in contact with a proximal portion of the hydraulic line 48. As known in the art, the pump 52 has a plurality of rollers 53 driven by a rotor 55 to compress the hydraulic line 48 against the pump bed 51 to advance fluid in the lumen of the hydraulic line 48.

Figure 2:
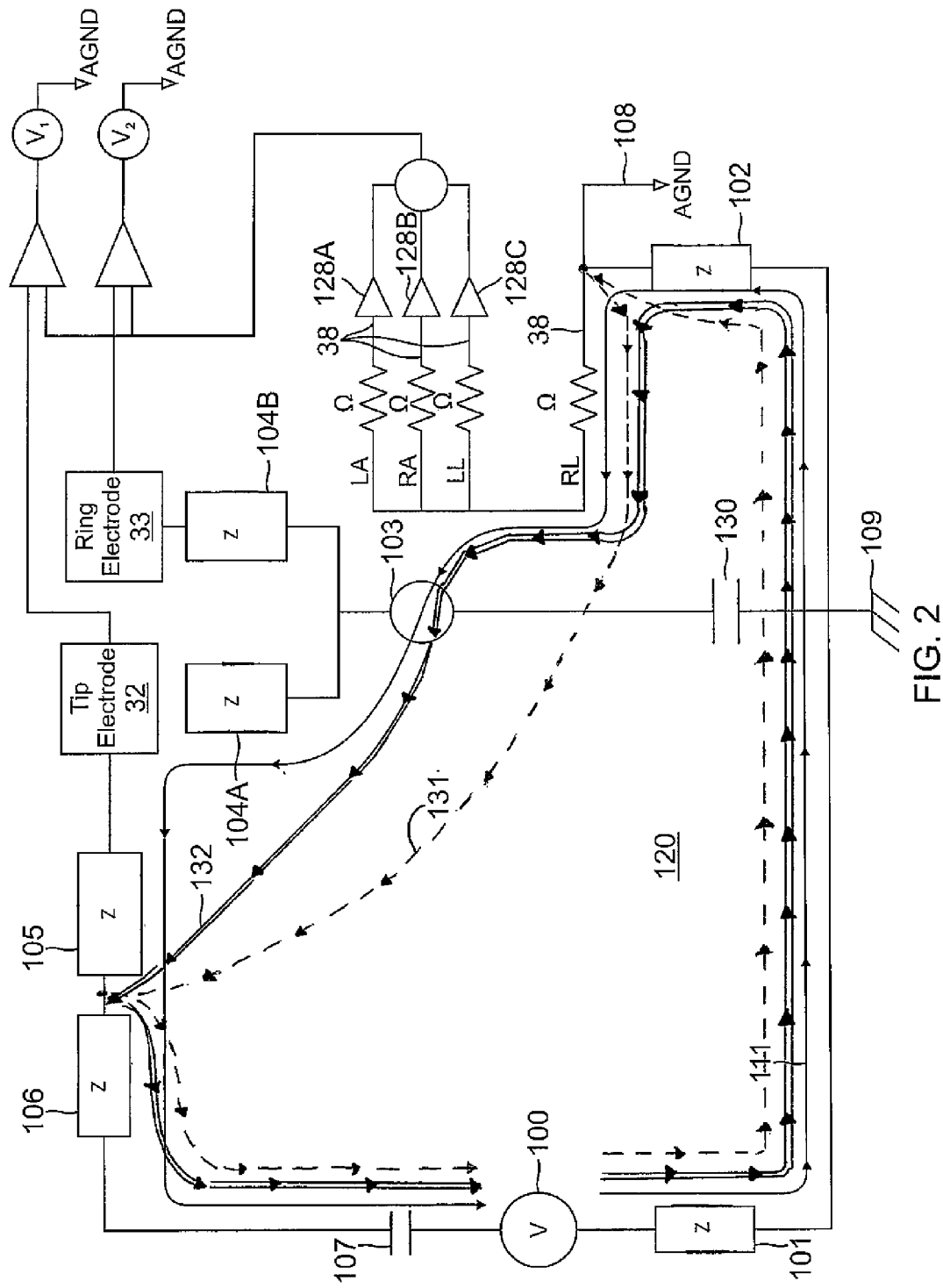
FIG. 2 is a schematic circuit diagram of selected electronics of the system of FIG. 1.

To better understand the triboelectric charging of the surface of the hydraulic line 48 and its translation into the measurable noise spikes on ECG recordings of the catheter electrode 32, reference is made to FIG. 2 which is a schematic circuit diagram representative of selected electrical circuits of the system 10, including a triboelectric noise source 100 applying a voltage across a circuit 120, that includes an impedance block 101 (representing impedance of the peristaltic pump bed 51/roller 53-to-actual ground 109), actual ground 109 of the console 24, an impedance block 102 (representing impedance of the console 24-to-analog ground 108), a patient ground 103, impedance blocks 104A and 104B (representing impedance of patient tissue to irrigated ablation electrode 32, and impedance of patient tissue to nonirrigated ring electrode 33, respectively), an impedance block 105 (representing impedance of saline inside catheter irrigation tubing 115), an impedance block 106 (representing impedance of saline inside hydraulic line 48), and capacitor 107 (representing tubing wall capacitive coupling of the hydraulic line 48). As such, noise introduced by the peristaltic pump 52 can be described as traveling along a pathway 111 (shown in solid line) affecting intracardiac ECG readings detected by irrigated electrode 32 and revealing itself as "spikes" in the electrocardiograms shown on the monitor 37 (FIG. 1).

The noise source modeled as the voltage source 100 corresponds to the potential created between the hydraulic line 48 and the pump bed 51 and between the hydraulic line 48 and the rollers 53 driven by a rotor 55 due to triboelectric charge. The noise is capacitively coupled to the conductive fluid, e.g., saline, through the tubing wall of the hydraulic line 48 (capacitor 107). It is understood that in the embodiment represented by FIG. 2, both the pump bed 51 and the rollers 53 are generally isolated from the actual ground 109, such that their impedances are also generally capacitive.

The voltage sampling in the console 24 is performed by differential amplifiers 128A, 128B and 128C, where the reference voltage is the sum of the ECG body surface patches 38LA, 38RA and 38LL. The ECG body surface patch 38 RL is shorted to analog ground 108 through a resistor 129

Inspecting the circuit of FIG. 2, the system 10 of the present invention offers pathways 131 (single dash) and 132 (double dash) as possible solutions to intracardiac ECG recording noise arising from the triboelectric charge. The system of the present invention recognizes that the circuit 120 can be closed through the ECG body surface patch 38RL and the isolation impedance of the console 24 (block 102). It may serve as an alternative or additional path for the triboelectric charge to travel for eliminating noise by eliminating the current travelling through tip and ring electrode. It is also assumed that no triboelectric current flows to the ECG body surface patches 38RA, 38LA, 38LL, 38LA, as they have unit gain buffers with very high input impedance.

The system further appreciates that for the pathway 111 which results in noise in the intracardiac ECG recordings, the triboelectric current flows through the irrigated catheter electrode 32, such that the noise is observed on the electrode 32 and no substantial noise is measured on the nonirrigated electrode 33. (It is understood that different catheters may exhibit different behavior, especially where it has irrigation at more than one catheter electrode.) The difference between the ablation electrode 32 and the ring electrode 33 is due to the irrigation holes of ablation electrode 32 allowing electrode 32 direct contact with the saline carrying the triboelectric charge from the pump 52. The nonirrigated ring electrode 33, on the other hand, is separated from the irrigated electrode 32 by relatively high impedance determined by a small surface area of the electrodes. It is understood that with a measured impedance of 100 Ohms (at 480 kHz), most of this impedance is located in the close vicinity of the electrode, while the rest of the saline volume in the patient tissue has much lower impedance. This observation allows the patient impedance to be modeled as two impedances, one from electrode 32 and one from electrode 33, to the common point referred to as patient ground 103.

Even without the exact values of the impedances, the system 10 of the present invention considers most of the circuit impedances of FIG. 2 to be dominated by capacitive component, such that the whole circuit has High-Pass behavior.

The noise may be measured on the patient tissue impedance which includes impedance block 104A (representing patient tissue impedance at irrigated electrode 32), which is relatively low in comparison to other impedances in the circuit, thus the noise voltage may be generally determined by the following relation:

$$V_{(ablation\ electrode)} = I_{noise} R_{Tissue/Body} \quad \text{(Eqn 1)}$$

where the noise current is determined by high impedances, for example, ground isolation, tubing wall impedance, saline in the lumen, etc.

Advantageously, the system 10 of the present invention recognizes alternate pathways for the triboelectric charge to travel, wherein the charge can avoid the tip of the catheter, including the irrigated ablation electrode 32, or any other electrodes on the catheter, including the nonirrigated ring electrode(s) 33. By electrically connecting the saline in the hydraulic line 48 at a location distal of the pump 52 and proximal of the catheter distal tip 18 to patient ground 103 (via, for example, a cable from hydraulic line connected to surface electrode patches 38) to provide pathway 132, or to analog ground 108 in the catheter 20 to provide 131, as shown in FIG. 2, the catheter, and its electrodes and reference patches (LA, RA, LL and RL) are excluded from the pathway of the triboelectric charge which results in significant noise reduction on intracardiac ECG recordings.

Figure 3:
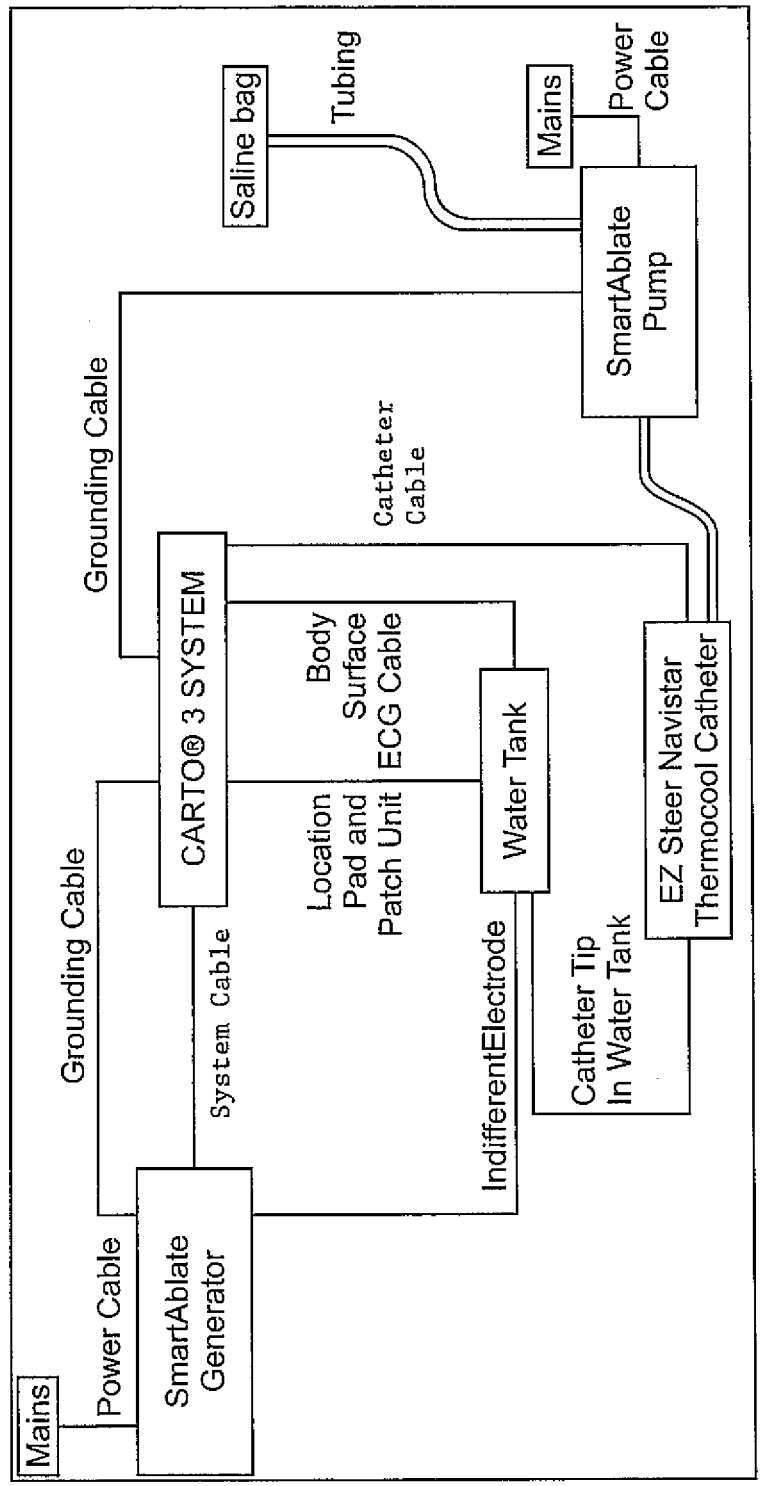
FIG. 3 is an ECG noise measurement experiment setup.
Figure 4A:
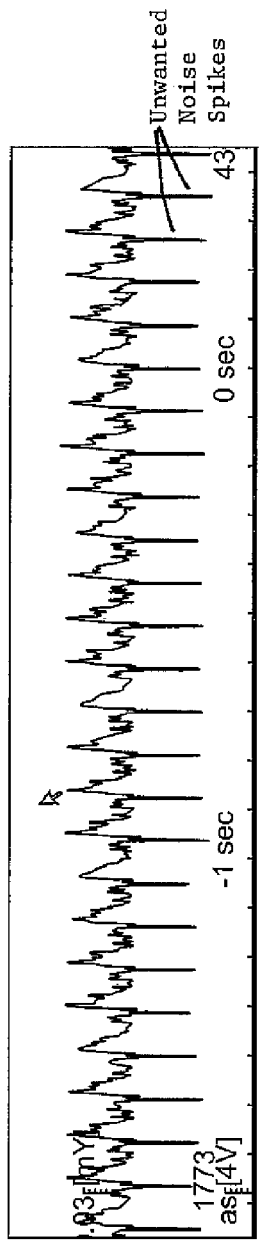
FIG. 4A is an ECG recording of the setup of FIG. 3, with no shorting of tribelectric charge.
Figure 4B:
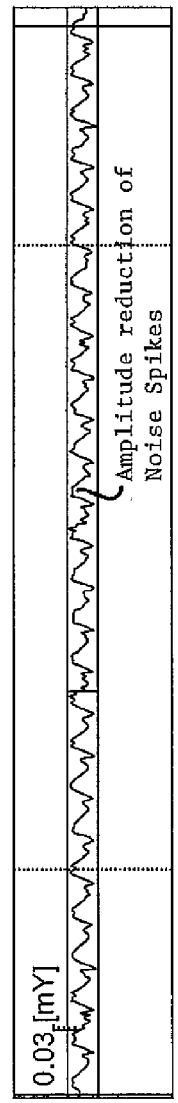
FIG. 4B is an ECG recording of the setup of FIG. 3, with shorting to patient ground.
Figure 4C:
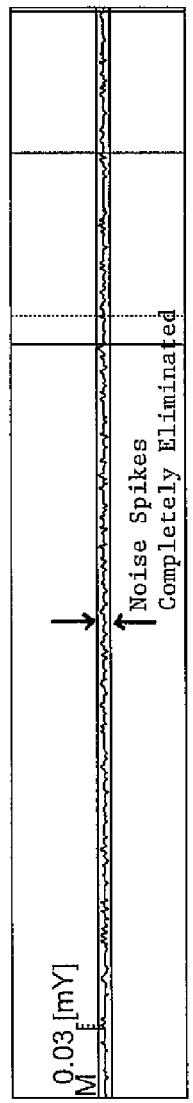
FIG. 4C is an ECG recording of the setup of FIG. 3, with shorting to analog ground.

An experiment with a nominal setup as illustrated in FIG. 3 was conducted with no grounding of the triboelectric charge. Accordingly, with the tribo electric current traveling along pathway 111 with no grounding (FIG. 2), intracardiac ECG recordings of FIG. 4A included noise "spikes" at about 150 µVp-p. In contrast, with the provision of an electrical connection or "short" between patient ground 103 and the saline in the hydraulic tubing 48, as shown by pathway 132 (double dash in FIG. 2), the noise spikes in FIG. 4B were significantly reduced to about 30 µVp-p. However, with the provision of an electrical connection or "short" between analog ground 108 and the saline in the hydraulic tubing 48, as shown by pathway 131 (single dash in FIG. 2), the noise spikes of FIG. 4C were further reduced down to about 10 µVp-p.

This experiment confirmed that grounding saline to either patient ground 103 (pathway 132) or the isolated analog ground 108 (pathway 131) reduces the measured noise below the required threshold. Notably, shorting saline to patient ground 103 (pathway 132) eliminates the noise spikes, but some residual low frequency noise remains, whereas shorting to analog ground 108 (pathway 131) can completely eliminate the noise. Shorting to the patient ground 103 does not eliminate noise because the quality of the intracardiac signal sensed by the catheter electrode 32 is dependent on the quality of the reference signal vis-à-vis ECG body surface patches 38RA, 38LA, 38LL, 38RL which are electrically connected to the patient ground 103.

It is understood that the electrical connection or "short" between the analog ground 108 and hydraulic line 48 (pathway 131) is not intended to affect intracardiac ECG signals, because the saline in the lumen of the hydraulic line 48 (a very small diameter) presents a very high impedance (generally of several mega-ohms) and thus, shorting the saline before it enters the catheter does not affect the impedances measured at the catheter distal tip 18.

In accordance with a feature of the present invention, an electrical connection that allows the applied voltage from the triboelectric noise source 100 to be grounded in a manner that bypasses the components of the system at least (1) receiving or in contact with the conductive fluid and (2) in electrical contact with the patient, including irrigated catheter electrode, can significantly reduce, if not eliminate, peristaltic pump noise in intracardiac ECG recordings.

In the illustrated embodiment of FIGS. 6A and 6B, the control handle 20 has barrel housing 63 including a proximal barrel extension 66 whose distal end is inserted in a proximal end of the barrel housing 63. Extending through the control handle 20 is the irrigation tubing 115 providing the lumen 44, whose proximal end includes a luer hub 117 adapted for fluid communication with the hydraulic line 48. Located at the proximal end of the barrel extension 66 is an electrical connector 119 that connects to the cable 34. The hollow barrel extension 66 houses a printed circuit board (PCB) 65 and associated microprocessor for storing and pre-processing data collected from the sensors 33. The cable 34 is a standard cable terminated on both ends with multi-pin connectors. The cable 34 connects to the console 24. As understood by one of ordinary skill in the art, the PCB 65 provides a pin 67 that is connected to the analog ground 108 (see FIG. 2). Because the catheter has electronics for measuring and processing body surface ECG signals as a reference signal for intracardiac ECG signals sensed by the catheter electrodes, the PCB 65 provides the pin 67 connected to the analog ground 108.

In accordance with a feature of the present invention, an electrical connection 110, for example, a wire or cable 112, upstream of electrical contacts or connection to the patient 13 allows the triboelectric current arising from interaction between the peristaltic pump 52 and the hydraulic line 48 and imparted to the fluid to avoid the patient 13. The wire or cable 112 linking the fluid and the PCB pin 67 provides an alternate electrical current pathway (pathway 131 in FIG. 2) for the triboelectric current to pass to the catheter's existing analog ground 108 via the cable 34, thereby avoiding the various catheter electrodes, including electrode 32, and thus the patient 13 who would otherwise come into contact with the catheter electrodes and the charged fluid. By bypassing and avoiding the patient 13, the triboelectric charge imparted to the fluid is rerouted to the analog ground 108 and diverted from producing. In some embodiments, the wire 112 is provided in the interior of the barrel housing of the control handle 20 and thus has a very short length to fit inside the control handle, as shown in FIG. 6B. One end of the wire 112 is electrically connected and affixed to the pin 67, for example, by welding and/or by conductive adhesive. The other end of the wire 112 extends through a hole formed in the side wall of the irrigation tubing 115 and into the lumen 44 to contact the fluid therein. The wire 112 is surrounded by a nonconductive tubing 113, and because the fluid is under pressure, the nonconductive tubing 113 is affixed to the irrigation tubing 115 and the PCB 56 by a sealant 114 to prevent leakage of the fluid into the interior of the control handle 20.

Figure 7:
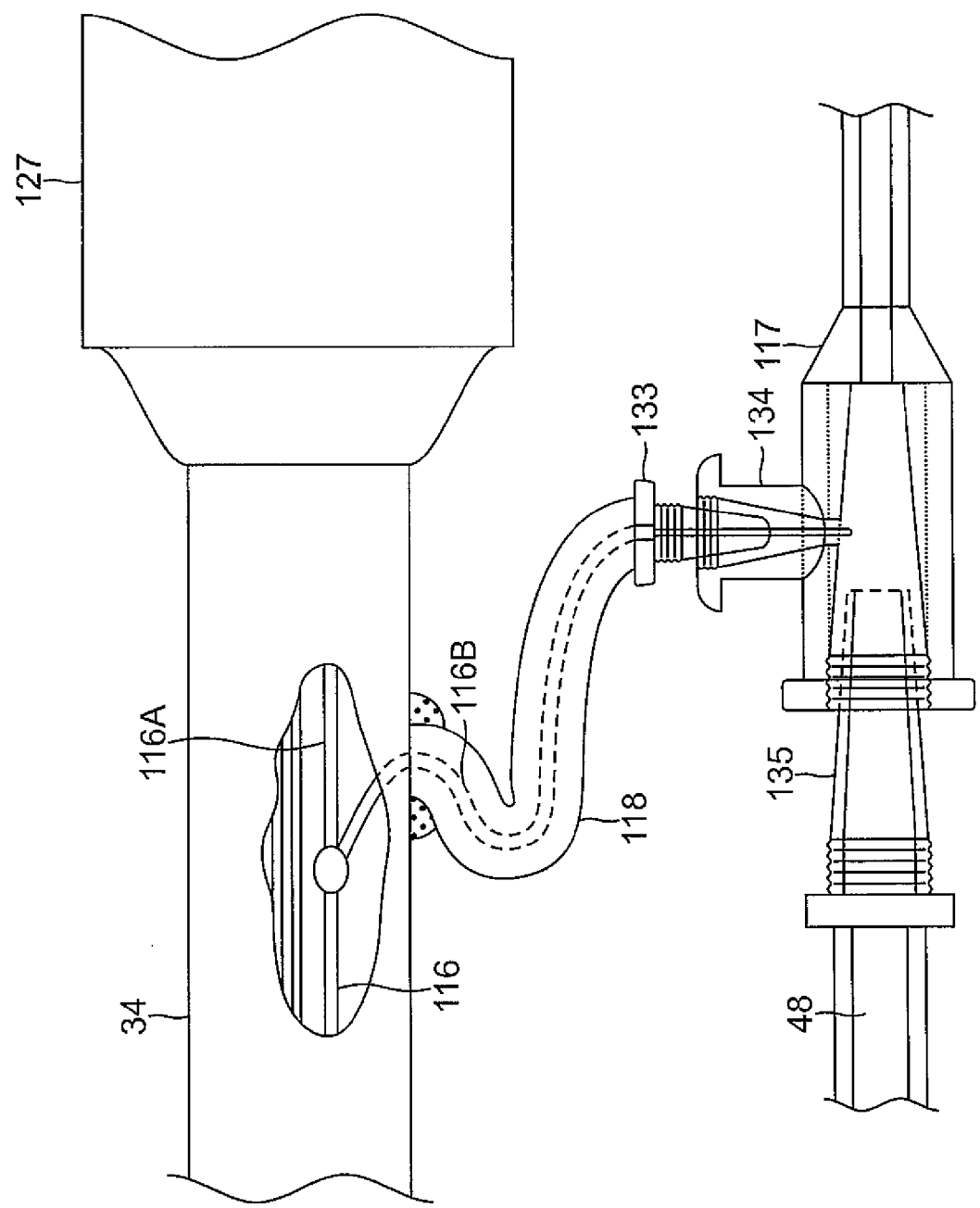
FIG. 7 is a detailed view of a distal end of a catheter cable in accordance with an embodiment of the present invention.
Figure 8A:
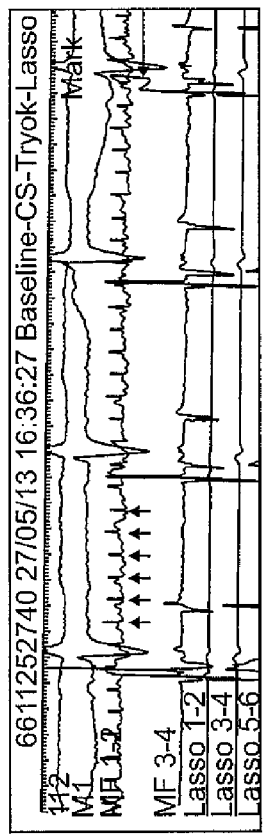
FIGS. 8A-8C are ECG recordings showing "noise" in a conventional catheterization system.
Figure 8B:
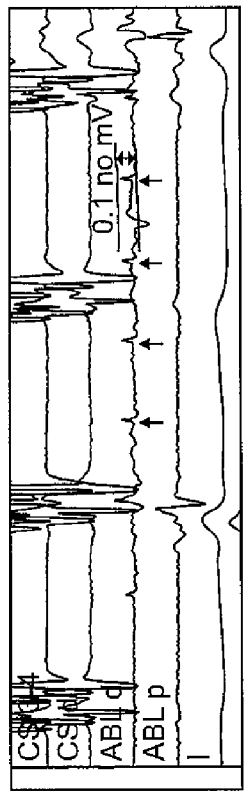
Figure 8C:
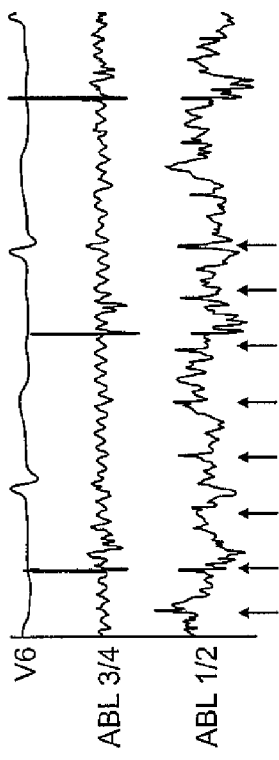

Alternately, the electrical connection 110 to the isolated analog ground 108 is provided outside and proximal of the control handle 20. In some embodiments, the system 10 includes a divergence of a wire 116 in the cable 34 that is adapted for connection to the PCB pin 67 in the control handle 20 via the electrical connector 119 at the proximal end of the control handle 20. As illustrated in FIG. 7, the wire 116 diverges or is split into first and second wires 116A and 116B. The first wire 116A continues to extend distally through the cable 34 to its distal connector 127 adapted to connect to the electrical connector 119 at the proximal end of the control handle 20. The second wire 116B has a distal end that extends into a male luer connector 133 adapted for connection with a side port 134 of the luer hub 117 in which the distal end of the hydraulic line 48 terminates proximally of the control handle 20. The wire 116B, which is made of a biocompatible and sterile material, passes through the male luer connector 133 and the side port 134, and into the lumen of the luer hub 117 where it comes into contact with fluid passing from the hydraulic line 48 having a male luer connector 135 that is adapted for connection to the irrigation tubing 115 of the catheter via the luer hub 117. Accordingly, the triboelectric current is rerouted from the lumen of the hydraulic line 48 to the wire 116B and proximally along the wire 116 in the cable 34 to the console 24, thus avoiding the electrodes of the catheter and the patient.

As discussed above, reported amplitudes of peristaltic pump noise "spikes" (measured peak to peak) can range generally between about 100-200 µV. With the system of the present invention wherein the applied voltage of the triboelectric effect is grounded to an analog ground 108 (FIG. 2) accessible via the PCB 65 in the catheter handle 20, the noise reduction is absolute and complete, to generally zero, limited by only the sensitivity of the ECG system, for example, about 10 µV, The present invention is not limited to the effects of triboelectric charge but rather the present invention can exclude any other noise that may occur due to hydraulic line, for example, mechanical pressure waves generated in tubing due to back pressure, mechanical pressure waves in catheter lumen due to back pressure, frictional noise, etc.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in some embodiments may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheterization system, comprising:
a catheter having a flexible catheter shaft with a distal portion adapted for insertion into a heart of a subject, the catheter shaft having a lumen for passing an electrically conductive fluid therethrough to exit the catheter at the distal portion;
a control handle at a proximal end of the catheter, the control handle providing an isolated ground of the system;
an electrical connection having first and second ends, the electrical connection linking the electrically conductive fluid and the isolated ground provided by the control handle, the first end of the electrical connection being in contact with the isolated ground provided by the control handle, and the second end of the electrical connection being in contact with the electrically conductive fluid at a location proximal to the distal portion of the catheter shaft.

2. The catheterization system of claim 1, wherein the second end of the electrical connection is in contact with the electrically conductive fluid in the lumen of the catheter shaft.

3. The catheterization system of claim 1, wherein the second end of the electrical connection is in contact with the electrically conductive fluid inside the control handle.

4. The catheterization system of claim 3, wherein the electrical connection includes an electrically conductive wire that is housed in the control handle and configured to provide electrical connection between the electrically conductive fluid and the isolated ground provided by the control handle.

5. The catheterization system of claim 1, wherein the second end of the electrical connection in contact with the electrically conductive fluid is proximal of the control handle.

6. The catheterization system of claim 5, wherein the electrical connection includes an electrically conductive wire having a divergence with one arm in electrical connection with the isolated ground provided by the control handle and another arm terminating inside a luer connector, the luer connector being configured for connection with the lumen of the catheter shaft for passing the electrically conductive fluid, and the luer connector being proximal of the control handle, the another arm adapted for electrical connection with the fluid passing through the lumen of the catheter shaft at a location proximal of the control handle.

7. The catheterization system of claim 1, wherein the isolated ground includes a pin located on a printed circuit board housed in the control handle.

8. The catheterization system of claim 7, wherein the electrical connection links the electrically conductive fluid and the pin.

9. The catheterization system of claim 8, wherein the electrical connection includes an electrically conductive wire extending between the electrically conductive fluid and the pin.

10. The catheterization system of claim 7, wherein the electrical connection linking the electrically conductive fluid and the pin is located inside the control handle.

11. The catheterization system of claim 10, wherein the electrical connection includes an electrically conductive wire extending between the electrically conductive fluid and the pin.

12. The catheterization system of claim 1, further comprising a fluid reservoir having a hydraulic line connected to the lumen to form fluid communication therewith.

13. A catheterization system, comprising:
a catheter having a flexible catheter shaft with a distal portion adapted for insertion into a heart of a subject, the catheter shaft having a lumen for passing an electrically conductive fluid therethrough to exit the catheter at the distal portion, the catheter having a control handle housing a printed circuit board having an isolated ground of the system, the isolated ground including a pin on the printed circuit board;
a fluid reservoir having a hydraulic line connected to the lumen to form fluid communication therewith; and
an electrical connection having first and second ends the electrical connection linking the electrically conductive fluid and the pin, the first end of the electrical connection being in contact with the pin on the printed circuit board and the second end of the electrical connection being in contact with the electrically conductive fluid at a location proximal to the distal portion of the catheter shaft.

14. The catheterization system of claim 13, wherein the electrical connection comprises an electrically conductive wire.

15. The catheterization system of claim 14, wherein the wire extends between the fluid and the pin.

16. The catheterization system of claim 14, wherein the wire has a portion extending in the lumen of the catheter.

17. The catheterization system of claim 13, wherein the hydraulic line includes a luer hub and the electrical connection includes a wire. the first end of the electrical connection being electrically connected to the pin and the second end terminating in a male luer connector connected to the luer hub, wherein the second end of the electrical connection extends into the luer hub in fluid communication with the lumen of the catheter.

18. The catheterization system of claim 17, wherein the first end of the electrical connection is electrically connected to the pin at a location proximal of the control handle.

* * * * *